United States Patent
McLaughlin et al.

(10) Patent No.: US 9,192,314 B2
(45) Date of Patent: Nov. 24, 2015

(54) PROBE FOR NEURAL RECORDING AND OPTICAL SPECTROSCOPIC INTERROGATION

(75) Inventors: Bryan McLaughlin, Cambridge, MA (US); John LeBlanc, North Andover, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 766 days.

(21) Appl. No.: 13/434,313

(22) Filed: Mar. 29, 2012

(65) Prior Publication Data

US 2012/0287420 A1    Nov. 15, 2012

Related U.S. Application Data

(60) Provisional application No. 61/468,842, filed on Mar. 29, 2011.

(51) Int. Cl.
*A61B 5/0478* (2006.01)
*A61B 5/04* (2006.01)
*A61B 5/00* (2006.01)
*A61N 5/06* (2006.01)

(52) U.S. Cl.
CPC ........... *A61B 5/04001* (2013.01); *A61B 5/0084* (2013.01); *A61B 5/6848* (2013.01); *A61B 5/6868* (2013.01); *A61N 5/0622* (2013.01); *A61B 2562/0233* (2013.01); *A61B 2562/046* (2013.01); *A61B 2562/12* (2013.01); *A61B 2562/226* (2013.01); *A61B 2562/227* (2013.01)

(58) Field of Classification Search
CPC ............... A61B 5/0084; A61B 5/0086; A61B 5/04001; A61B 5/0478; A61B 5/0484; A61B 5/40; A61B 5/4041; A61B 5/4058–5/407; A61B 5/4893; A61B 5/6846; A61B 5/6847; A61B 5/6848; A61B 5/6868; A61B 5/6877; A61B 2562/0238; A61B 2562/0233; A61B 2562/066
USPC .......................................... 600/373, 377, 378
See application file for complete search history.

(56) References Cited

U.S. PATENT DOCUMENTS 6,048,359 A * 4/2000 Biel ............................... 607/92
2002/0045832 A1   4/2002 Giller et al.
(Continued)

FOREIGN PATENT DOCUMENTS

WO    WO-2011068696 A2    6/2011

OTHER PUBLICATIONS

A New Class of Chronic Recording Multichannel Neural Probes With Post-Implant Self-Deployed Satellite Recording Sites; Daniel Egert and Khalil Najafi, WIMS; Univ. of Michigan, (2011).

(Continued)

*Primary Examiner* — Linda Dvorak
*Assistant Examiner* — Erin M Cardinal
(74) *Attorney, Agent, or Firm* — Edward A. Gordon; Foley & Lardner LLP

(57) ABSTRACT

In various embodiments, a probe includes at least one shank, optical components disposed within the shank for transmitting light into a sample and collecting light from the sample, and electrical components disposed within the shank for recording an electrical signal from the sample. In certain embodiments, a method includes collecting light from the sample using a first shank of the probe, recording an electrical signal from the sample using a second shank of the probe, and analyzing the collected light and the electrical signal.

12 Claims, 13 Drawing Sheets

(56) References Cited

U.S. PATENT DOCUMENTS

| | | | |
|---|---|---|---|
| 2003/0091289 A1* | 5/2003 | Saito et al. ............... | 385/49 |
| 2004/0006274 A1* | 1/2004 | Giller et al. ............... | 600/473 |
| 2008/0077200 A1* | 3/2008 | Bendett et al. ............. | 607/89 |
| 2009/0118800 A1 | 5/2009 | Deisseroth et al. | |
| 2009/0177144 A1 | 7/2009 | Masmanidis et al. | |
| 2009/0210039 A1* | 8/2009 | Boyden et al. ............. | 607/89 |
| 2010/0016732 A1 | 1/2010 | Wells et al. | |
| 2010/0022861 A1* | 1/2010 | Cinbis et al. .............. | 600/325 |
| 2011/0024771 A1 | 2/2011 | Hajj-Hassan et al. | |
| 2011/0060377 A1 | 3/2011 | Howard | |
| 2011/0106206 A1 | 5/2011 | Schiff | |
| 2011/0112591 A1 | 5/2011 | Seymour et al. | |
| 2011/0208031 A1 | 8/2011 | Wolfe et al. | |
| 2011/0295331 A1 | 12/2011 | Wells et al. | |
| 2011/0295347 A1* | 12/2011 | Wells et al. .............. | 607/89 |
| 2012/0035583 A1 | 2/2012 | Sepkuty | |
| 2012/0089205 A1* | 4/2012 | Boyden et al. ............. | 607/88 |
| 2013/0030274 A1* | 1/2013 | Jamieson et al. .......... | 600/377 |

OTHER PUBLICATIONS

A Microprobe with Integrated Amplifiers for Neurophysiology; K.D. Wise and J.B. Angell; Session IX: Integrated Electronics in Biomedicine; THAM 9.1; ISSCC 71 Stanford Univ., CA., (1971).

On the Design of Multi-Site Microelectrodes for Neuronal Recordings; U. G. Hofmann, et al.; Micro Tec 2000, Hanover, Germany.

Hajj-Hassan Metal: Brain machine interfaces combining microelectrode arrays with nanostructured optical biochemical sensors II. Proceedings of the SPIE—The International Society for Optical Engineering SPIE—The International Society for Optical Engineering USA, vol. 7188, 2009, XP002676682.

Il-Joo Cho et al: "A 16-site neural probe integrated with a waveguide for optical stimulation". 23rd IEEE International Conference on Micro Electro Mechanical Systems (MEMS 2010) IEEE Piscataway, NJ, USA, 2010, pp. 995-998, XP002676681.

International Search Report in PCT/US2012/031232 dated Jun. 11, 2012.

Royer Sebastien et al: "Multi-array silicon probes with integrated optical fibers: light-assisted perturbation and recording of local neural circuits in the behaving animal." The European Journal of Neuroscience Jun. 2010 LNKD-PUBMED:20529127, vol. 31, No. 12, Jun. 2010, pp. 2279-2291, XP002676683.

Zhang J et al: "A microelectrode array incorporating an optical waveguide device for stimulation and spatiotemporal electrical recording of neural activity". Proceedings of the 31st Annual International Conference of the IEEE Engineering in Medicine and Biology Society: Engineering the Future of Biomedicine, EMBC 2009—Proceedings of the 31st Annual International Conference of the IEEE Engineering in Med, 2009, pp. 2046-2049, XP002676680.

* cited by examiner

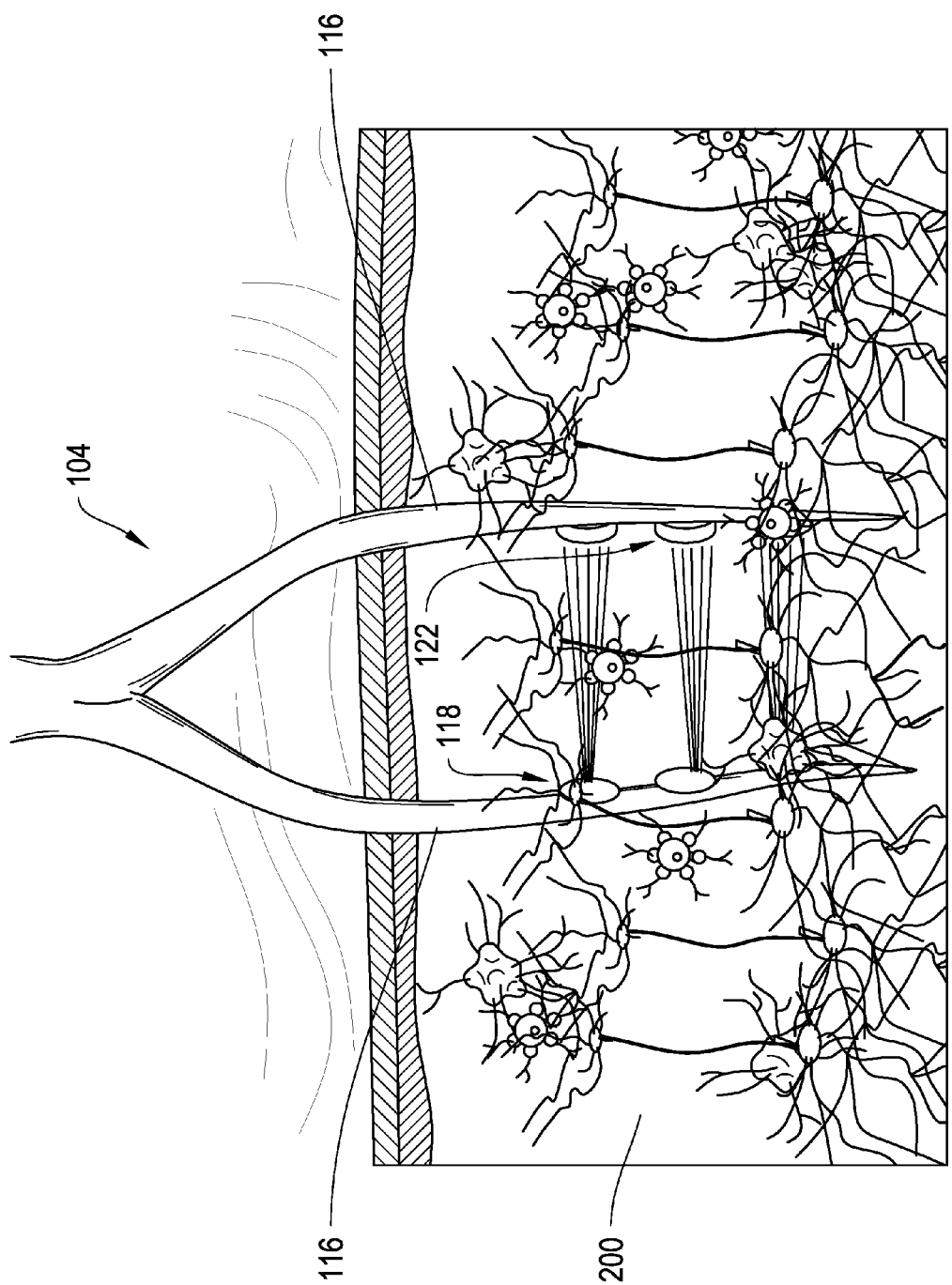

PROBE FOR NEURAL RECORDING AND OPTICAL SPECTROSCOPIC INTERROGATION

CROSS-REFERENCE TO RELATED APPLICATION

This application claims priority to and the benefit of, and incorporates herein by reference in its entirety, U.S. Provisional Patent Application No. 61/468,842, which was filed on Mar. 29, 2011.

TECHNICAL FIELD

In various embodiments, the invention relates to devices for stimulating and recording bioelectrical and optical spectroscopic activity. In particular, embodiments of the invention relate to small-scale, implantable probes for electrically and/or optically stimulating and recording neural activity.

BACKGROUND

Electrical stimulation and recordation of neural tissue may be performed by implanting into the tissue a device that includes an electrical lead having one or more electrodes. Typically, the lead is coupled to a signal generator that delivers electrical energy through the electrodes to the neural tissue, thereby stimulating an increase, decrease, or block of neuronal activity. The electrical response of the neural tissue may be measured and recorded.

Optical techniques may also be used for stimulating, monitoring, inhibiting, and/or modulating neural activity. Photostimulation, for example, may include various modes of interaction between light and the target neurons, including a variety of photo-physical and photo-biochemical effects, with various intrinsic components or exogenous sensitizers.

Devices for such purposes have received increasing attention from researchers and clinicians, especially as biomaterials and the technology of microscale probes and electronics have improved. Existing devices, however, are incapable of performing a desired combination of optical and electrical interrogation and/or recordation. Further, implantation of such devices may cause tissue damage and scar tissue buildup, which existing devices and methods are incapable of adequately detecting and monitoring.

Accordingly, there is a need for an improved, small-scale neurological device for electrically and/or optically stimulating and recording neural activity.

SUMMARY OF THE INVENTION

In various embodiments, the present invention features a probe or optrode for optically and electrically stimulating and recording neural activity. The optrode achieves this by combining optical components (e.g., waveguides) with electrical components (e.g., recording electrodes) in a single probe. For example, the optrode may include an optical waveguide embedded within an electrode substrate. The configuration allows the probe to provide optical spectroscopic interrogation and optical spectroscopic collection, in addition to neural recordation and/or bioimpedance measurements. In various embodiments, optical measurements are performed to monitor tissue damage and scar tissue buildup that may occur during and following implantation of the optrode. The optrode has a wide-range of biological applications, including, for example, treatment of Parkinson's disease, epilepsy, depression, obesity, hypertension, and heart disease. The optrode may also be used for cortical recording studies, for example, involving brain-computer-interfaces.

In general, in one aspect, embodiments of the invention relate to a probe. The probe includes at least one shank, optical components disposed within the at least one shank, and electrical components (e.g., an electrode) disposed within the at least one shank. The optical components are for transmitting light into a sample (e.g., neural tissue) and/or collecting light from the sample. The electrical components are for recording an electrical signal from the sample.

In certain embodiments, the optical components include at least one waveguide for transmitting light through the at least one shank. The waveguide may include, for example, a photodefinable polymer. In one embodiment, the optical components are in optical communication with one or more apertures defined by the at least one shank. In various embodiments, the electrical components are configured to apply a voltage to the sample and detect an electrical response of the sample. A width and a depth of the at least one shank is each preferably between about 10 microns and about 100 microns. For example, the width may be about 25 microns and the depth may be about 10 microns. In some embodiments, the at least one shank includes two shanks. A separation distance between the two shanks is preferably between about 20 microns and about 1000 microns (e.g., about 100 microns, or about 200 microns).

In general, in another aspect, embodiments of the invention relate to a system. The system includes a light source, a probe, a photo-detector, and a plurality of waveguides (e.g., external waveguides). The waveguides are for transmitting light from the light source to the probe and from the probe to the photo-detector. The probe includes at least one shank, optical components disposed within the at least one shank, and electrical components disposed within the at least one shank. The optical components are for transmitting light into a sample and collecting light from the sample. The electrical components are for recording an electrical signal from the sample. In certain embodiments, the electrical components are further configured to apply a voltage to the sample and detect an electrical response of the sample.

In general, in another aspect, embodiments of the invention relate to a method. The method includes collecting light from a sample, recording an electrical signal from the sample, and analyzing the optical characteristics of the collected light and the electrical signal to determine a health of the sample and/or neural activity within the sample. The light is collected using an optical component that is disposed within a first shank of a probe. The electrical signal is recorded using an electrical component that is disposed within a second shank of the probe.

In certain embodiments, the first and second shanks are the same shank or different shanks. The recording step may include detecting an electrical response to an applied voltage.

These and other objects, along with advantages and features of the embodiments of the present invention herein disclosed, will become more apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIG. 4 is a schematic front view of an optrode transmitting light through cortical neural tissue, in accordance with one embodiment of the invention;

DESCRIPTION

It is contemplated that devices, systems, methods, and processes of the claimed invention encompass variations and adaptations developed using information from the embodiments described herein. Adaptation and/or modification of the devices, systems, methods, and processes described herein may be performed by those of ordinary skill in the relevant art.

Throughout the description, where devices and systems are described as having, including, or comprising specific components, or where processes and methods are described as having, including, or comprising specific steps, it is contemplated that, additionally, there are devices and systems of the present invention that consist essentially of, or consist of, the recited components, and that there are processes and methods according to the present invention that consist essentially of, or consist of, the recited processing steps.

It should be understood that the order of steps or order for performing certain actions is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Various embodiments of the present invention feature an optrode probe for optically and/or electrically stimulating and/or recording neural tissue. The optrode may include a plurality of prongs or shanks configured to be inserted or implanted into neural tissue, such as skin tissue, brain tissue, or spinal tissue. Light and electricity may be transmitted through the shanks, and the optical and electrical response of the neural tissue between or around the shanks may be detected by the optrode and analyzed. In certain embodiments, the optrode is used to provide optical and/or electrical stimulation and neural monitoring in clinical applications (e.g., treatment of Parkinson's disease, epilepsy, depression, obesity, hypertension) and/or in research applications (e.g., treatment and/or diagnosis).

Figure 1:
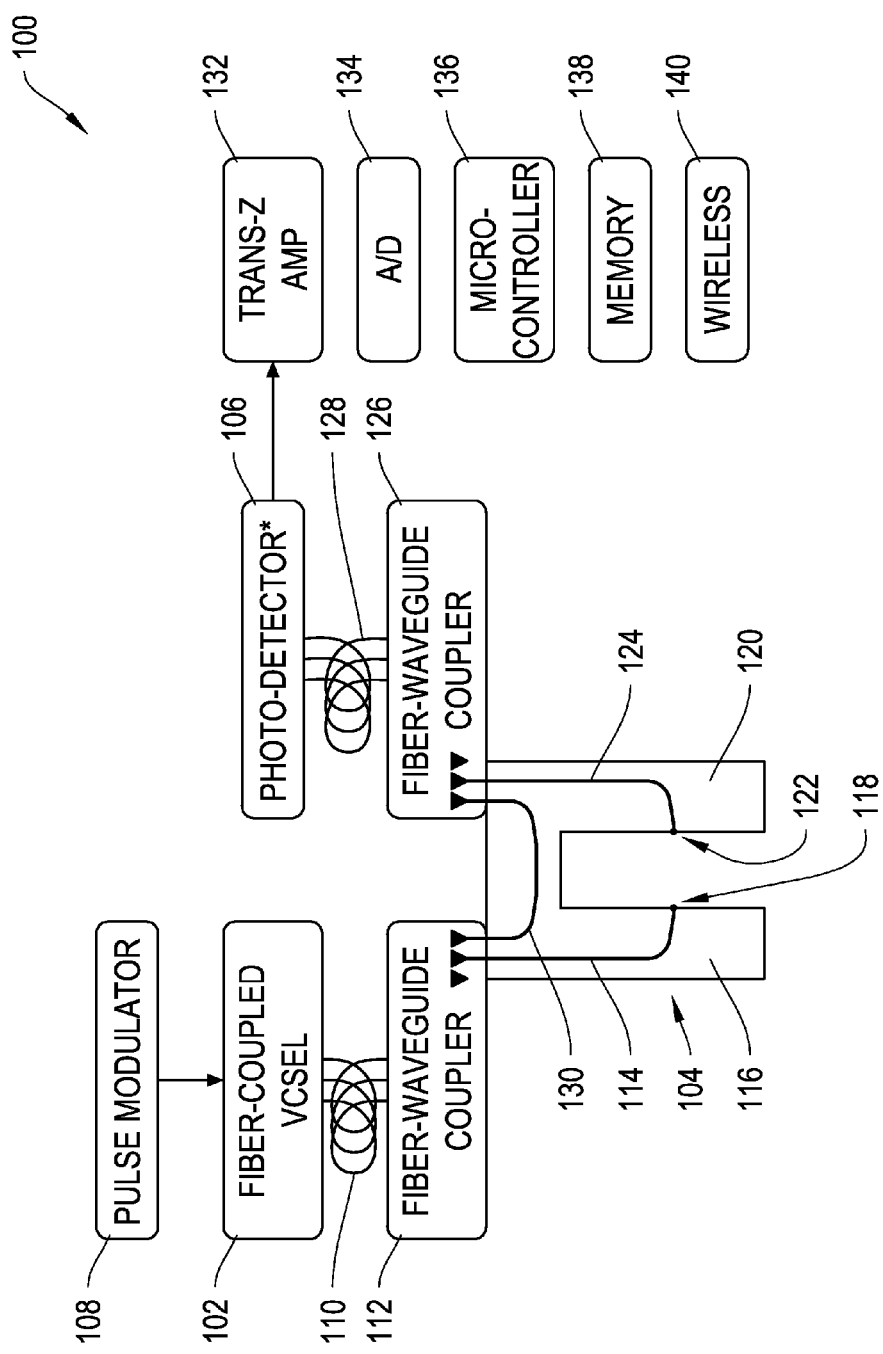
FIG. 1 is a schematic view of an optrode system, in accordance with one embodiment of the invention.

FIG. 1 depicts one embodiment of an optrode system 100 that includes a light source 102, an optrode 104, and a photo-detector 106. The light source 102 may include any light generation source, such as a laser, a laser diode, a vertical cavity surface-emitting laser (VCSEL), a light emitting diode, a fluorescent bulb, or an incandescent bulb. The light source may be, for example, an internal light source (i.e., located within the optrode 104) or an external light source (i.e., located outside the optrode 104). A pulse modulator 108 may be used to deliver a specified pattern of light pulses or other variations from the light source 102. Typical wavelengths generated by the light source 102 are visible to near-infrared (e.g., from about 400 nm to about 1000 nm). As depicted, the light source 102 is connected to the optrode 104 using one or more external waveguides 110 and waveguide couplers 112. Light from the light source 102 travels through the one or more external waveguides 110 and waveguide couplers 112 into the optrode 104. The optrode 104 includes one or more internal waveguides 114 to direct the light into a transmitting shank 116 of the optrode 104. The transmitting shank 116 includes one or more apertures 118, which receive the light from the internal waveguides 114 and direct the light into adjacent neural tissue.

In certain embodiments, at least a portion of the light emitted by the apertures 118 of the transmitting shank 116 is transmitted through the tissue and collected by a receiving shank 120 of the optrode 104. Like the transmitting shank 116, the receiving shank 120 includes one or more apertures 122 and internal waveguides 124 for collecting the light and transporting it through the receiving shank 120. One or more waveguide couplers 126 and external waveguides 128 receive the collected light from the internal waveguides 124 and deliver the light to the photo-detector 106. The photo-detector 106 measures and analyzes the characteristics of the collected light. For example, the photo-detector 106 may determine the intensity and/or the spectrum of the collected light.

In the depicted embodiment, the optrode 104 includes a calibration waveguide 130 to allow light to pass directly from the light source 102 to the photo-detector 106, without first passing through the neural tissue. The calibration waveguide 130 enables the photo-detector 106 to directly view the light from the light source 102 and thereby account for variations in the light that may occur over time (e.g., due to drift or power variations). In alternative embodiments, a calibration waveguide is formed as a bifurcation of an internal waveguide. For example, the internal waveguide 114 receiving light from the light source 102 may include a bifurcation or branch that travels directly to the waveguide coupler 126 connected to the photo-detector 106.

In certain embodiments, light from the light source 102 is directed into the optrode 104 using one or more lenses (e.g., a spherical lens, a biconvex lens, and/or a plano-convex lens) to collect and/or focus the light. The one or more lenses may be incorporated, for example, into one or more of the waveguides and/or waveguide couplers 112, 126. In one embodiment, a butt coupling is used to couple the light source 102 and the optrode 104. Any suitable coupling may be used to direct light from the light source 102 into the optrode 104.

In certain embodiments, the apertures 118, 122 and/or internal waveguides 114, 124 include a light directing element that directs light away from the transmitting shank 116 (e.g., in a direction perpendicular to a longitudinal axis of the transmitting shank 116). The light directing element may include one or more components that refract, reflect, focus, scatter, and/or perform any suitable manipulation of light. For example, the light directing element may include a reflector (e.g., a mirror) and/or a lens. The lens may be used to focus light to a point away from the transmitting shanks 116, 120. In one embodiment, the lens has a focal length preselected to focus light on targeted tissue or on the receiving shank 120. The focal length may be adjustable and/or variable to enable the lens to focus light at an adjustable distance away from the transmitting shank 116, thereby providing an improved ability to target particular tissue locations.

In various embodiments, the light directing element includes or is a diffuser. The diffuser scatters the light in all or several directions or angles when the light exits the transmitting shank 116. The diffuser may include, for example, a collection of particles dispersed in a medium (e.g., a glue or polymer). The diffuser may be a frost coating or covering.

In some embodiments, the optical components (e.g., the apertures 118, 122 and/or internal waveguides 114, 124) of the optrode 104 include a filter that allows only particular wavelengths of light to pass. For example, in some embodiments it may be desirable to interrogate neural tissue with a certain color or wavelength. A filter allowing that color or wavelength to pass may be utilized in this instance to achieve the desired interrogation.

In various embodiments, the optical components of the optrode 104 are selected and configured to transmit light into and/or receive light from the neural tissue. The light source 102 may be, for example, a vertical-cavity surface-emitting laser (VCSEL), such as the VCSEL-780, made by Thorlabs, Inc., of Newton, N.J. Each external waveguide 110, 128 may be a fiber optic waveguide. The waveguide couplers 112, 126 may include, for example, a V-groove fiber-waveguide coupler, made by Oz Optics, Ltd., of Ottawa, Ontario. In one embodiment, the photo-detector 106 is a spectrometer, such as the HR2000 made by Ocean Optics, Inc., of Dunedin, Fla. The pulse modulator 108 may be, for example, a laser diode driver, such as a Picosecond Light Pulser, made by Hamamatsu Photonics, of Japan.

In certain embodiments, the pulse modulator 108 is used to output light pulses that have a duration from about 1 picosecond to about 1 millisecond. For example, the duration of the pulses may be from about 1 nanosecond to about 100 nanoseconds. The light pulses may be intensity modulated (e.g., with a modulation frequency from about 50 MHz or less to about 1 GHz or more). The light pulses may have any shape, including, for example, square, triangular, saw-tooth, ramped up, or ramped down.

In some embodiments, the light from the light source 102 is not pulsed. For example, a continuous wave light may be used for steady-state recordings. In such instances, the pulse modulator 108 is not used and/or is not included in the optrode system 100.

As depicted, the optrode system 100 may also include a trans-impedance amplifier 132 (e.g., with positive or negative feedback, bias, and offset circuitry), an analog-to-digital converter 134, a microcontroller 136, computer memory 138, and/or a wireless components 140 (e.g., to achieve a wireless connection). In various embodiments, these items are used to deliver light pulses, collect captured light spectrographically, record or store data, process data (e.g., analyze data received from the optrode 104), and transmit data wirelessly to a networked device (e.g., a remote personal computer or workstation). Some or all of these items may be incorporated onto a circuit board that interfaces with the optical and electrical components of the optrode 104. The circuit board may be located, for example, inside the optrode 104 and/or outside the optrode 104, either partially or completely.

Although not explicitly shown in FIG. 1, in certain embodiments, the optrode system 100 also includes electrical components for electrically stimulating the neural tissue and/or receiving electrical signals from the neural tissue. The electrical components may include, for example, an electrical power source, at least one electrode in one or both of the transmitting shank 116 and the receiving shank 120, and/or a voltmeter or other device (e.g., a data acquisition system) for recording and/or measuring electrical signals received from the neural tissue. In one embodiment, the power source provides a voltage between two or more electrodes. Like the optical input, the electrical input from the power source may be pulsed or modulated over time.

Figure 2:
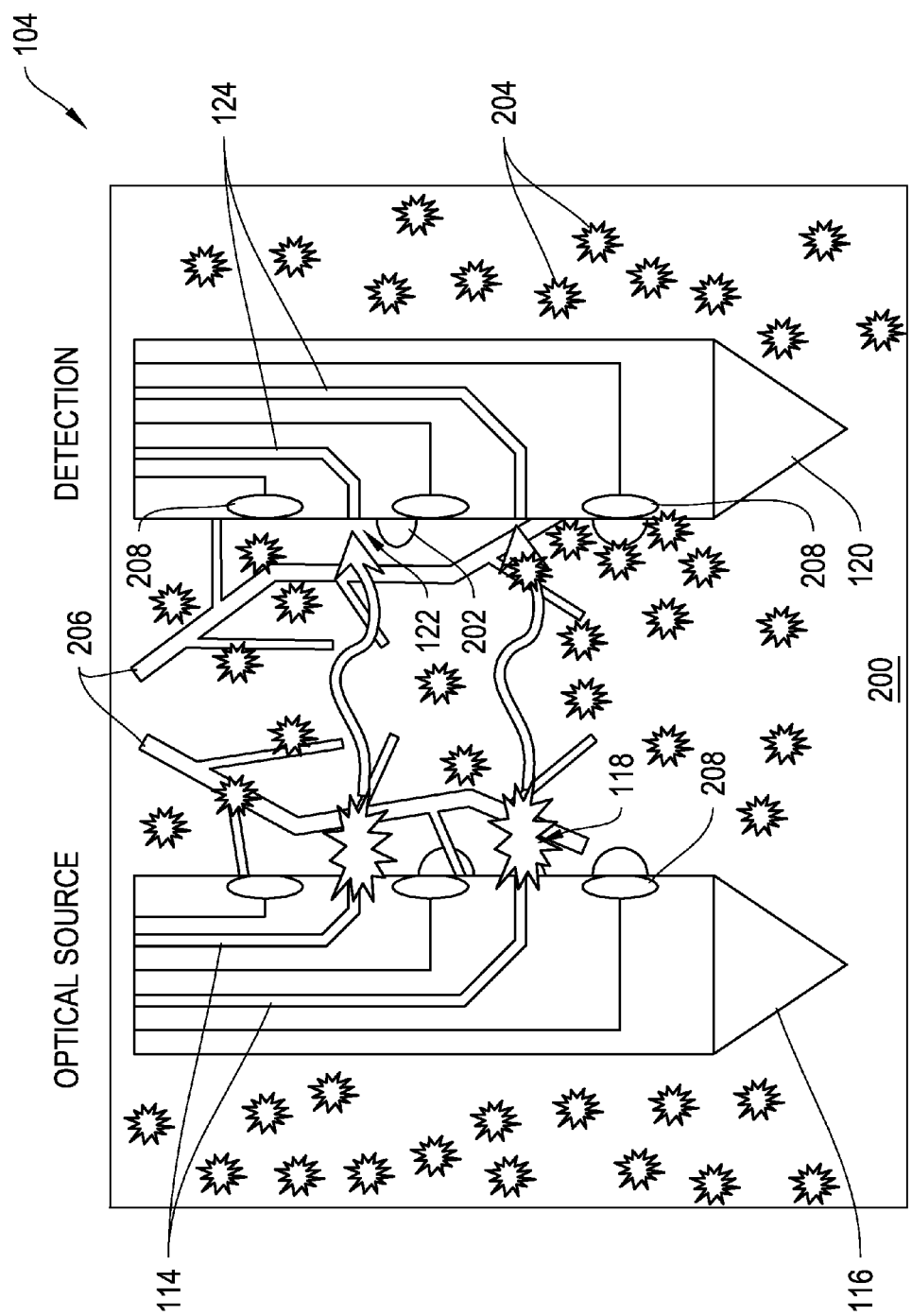
FIG. 2 is a schematic front view of an optrode inserted into cortical neural tissue, in accordance with one embodiment of the invention.

FIG. 2 is a schematic front view of the optrode 104 inserted into a sample of neural tissue 200, in accordance with one embodiment of the invention. The neural tissue 200 includes microglia 202, astrocytes 204, and cortical blood vessels 206. As depicted, the transmitting shank 116 and the receiving shank 120 include a plurality of internal waveguides 114, 124 and apertures 118, 122 for transmitting and/or receiving light. The transmitting shank 116 includes two internal waveguides 114 and two apertures 118, which direct light into the neural tissue 200 towards the receiving shank 120. The receiving shank 120 includes two corresponding internal waveguides 124 and apertures 122 for receiving light from the tissue 200 and transmitting the light to the photo-detector 106. In the depicted embodiment, the transmitting shank 116 and the receiving shank 120 also include a plurality of electrode sites or electrodes 208. The electrodes 208 are used to stimulate the tissue 200 and/or record electrical signals received from the tissue 200. Recording may be performed with or without optical or electrical stimulation. In one embodiment, an electrode 208 in one shank (e.g., the transmitting shank 116) is connected to a power source or a recording amplifier, while an electrode 208 in the other shank (e.g., the receiving shank 120) is connected to ground or a recording amplifier. A voltage difference between the two shanks 116, 120 may be detected and recorded.

The optrode shanks 116, 120 may be made of any solid material that provides the desired mechanical, electrical, and optical properties. In certain embodiments, the optrode shanks 116, 120 are made of silicon or a flexible polymer, such as polyimide. The internal waveguides 114, 124 may include one or more glasses, resins, polymers, and/or semiconductors. For example, the internal waveguides 114, 124 may include a photodefinable polymer or resin, such as polytetrafluoro-ethylene (TFE), chlorotrifluoro-ethylene (CTFE), acrylic, polypropylene, polybutylene, polyethylene, polystyrene, and polysulfone. In some embodiments, the internal waveguides 114, 124 include organic materials such as SU-8, Poly(methyl methacrylate) (PMMA), perfluoropolymers, polydimethylsiloxane (PDMS), and parylene, and/or inorganic materials such as silicon dioxide ($SiO_2$), silicon nitride, silicon oxynitride, and silica.

Figure 3A:
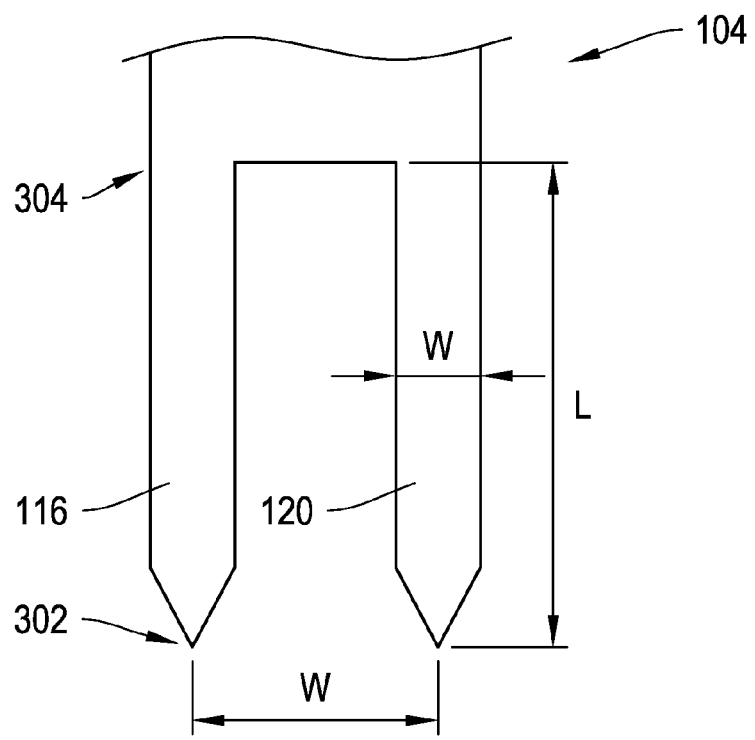
FIG. 3a is a schematic front view of optrode, in accordance with one embodiment of the invention.
Figure 3B:
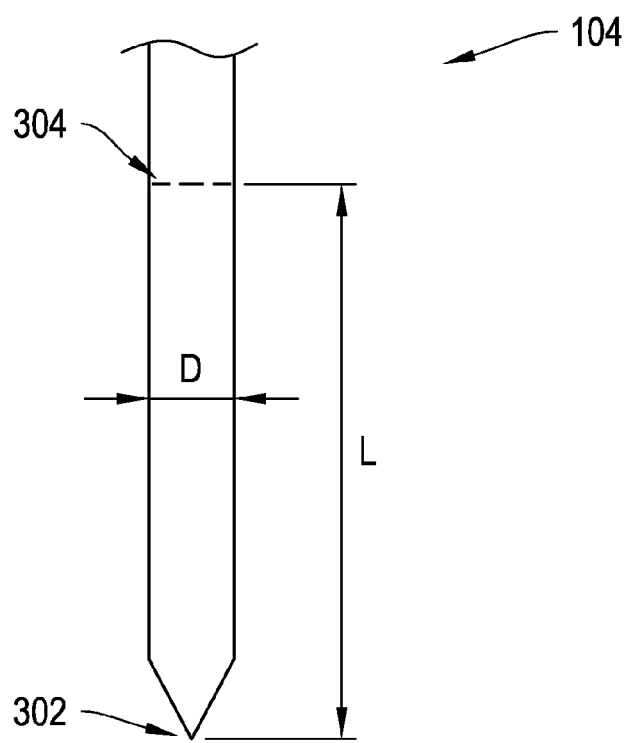
FIG. 3b is a schematic side view of the optrode of FIG. 3a, in accordance with one embodiment of the invention.

Referring to FIGS. 3a and 3b, in certain embodiments, the two shanks 116, 120 of the optrode 104 are separated by a shank separation distance X and have a rectangular cross-section. The shank separation distance X may be between about 20 microns and about 1000 microns, for example about 100 microns or about 200 microns. The shank separation distance X may be uniform or it may vary from a tip 302 of the shanks 116, 120 to a base 304 of the shanks 116, 120. In the depicted embodiment, the shanks 116, 120 have a rectangular cross-section with a width W and a depth D that are each between about 10 microns and about 100 microns. The width W of each shank is preferably about 25 microns and the depth D of each shank is preferably about 10 microns. In alternative embodiments, the shanks 116, 120 may have any cross-sectional shape, including hexagonal, triangular, circular, or oval. A length L of the shanks 116, 120 may be from about 100 microns to about 3000 microns. In one embodiment, the length L of the shanks 116, 120 is about 1000 microns. In one embodiment, the shanks 116, 120 are tapered, narrowing towards the tip 302, to reduce tissue damage during insertion into the tissue 200. The optrode 104 may be flexible or rigid.

Referring now to FIG. 4, the optrode 104 includes, in one embodiment, three apertures 118 on the transmitting shank 116 and three apertures 122 on the receiving shank 120. During operation of the optrode 104, light exits the apertures 118 on the transmitting shank 116, passes through the neuronal tissue 200, and is collected by the apertures 122 on the receiving shank 120. The configuration allows the optrode 104 to sense changes in tissue morphologies between the two shanks 116, 120. For example, as scar tissue accumulates in the tissue 200 over time, the amount of light received by the receiving shank 120 may change.

In certain embodiments, an optrode features a reflectance configuration where source and collection apertures are located on a single shank. For example, a shank may include an aperture for transmitting light into the tissue and an aperture for receiving light reflected by the tissue. Some combination of transmittance and reflectance is also possible. For example, depending on the configuration of the waveguides and apertures, the light received by a shank may come from both the same shank (i.e., reflectance) and a different shank (i.e., transmittance). The received light may also come from a source outside of the optrode (e.g., an external light source) and/or be generated within the tissue (e.g., due to fluorescence). For example, in one embodiment, the tissue emits light (e.g., fluoresces) when exposed to light and/or electricity. In some embodiments, the tissue emits electrical signals when exposed to light and/or electricity. The tissue may be genetically modified to achieve a desired electrical and/or optical response to the electrical and/or optical stimulation.

Figure 5:
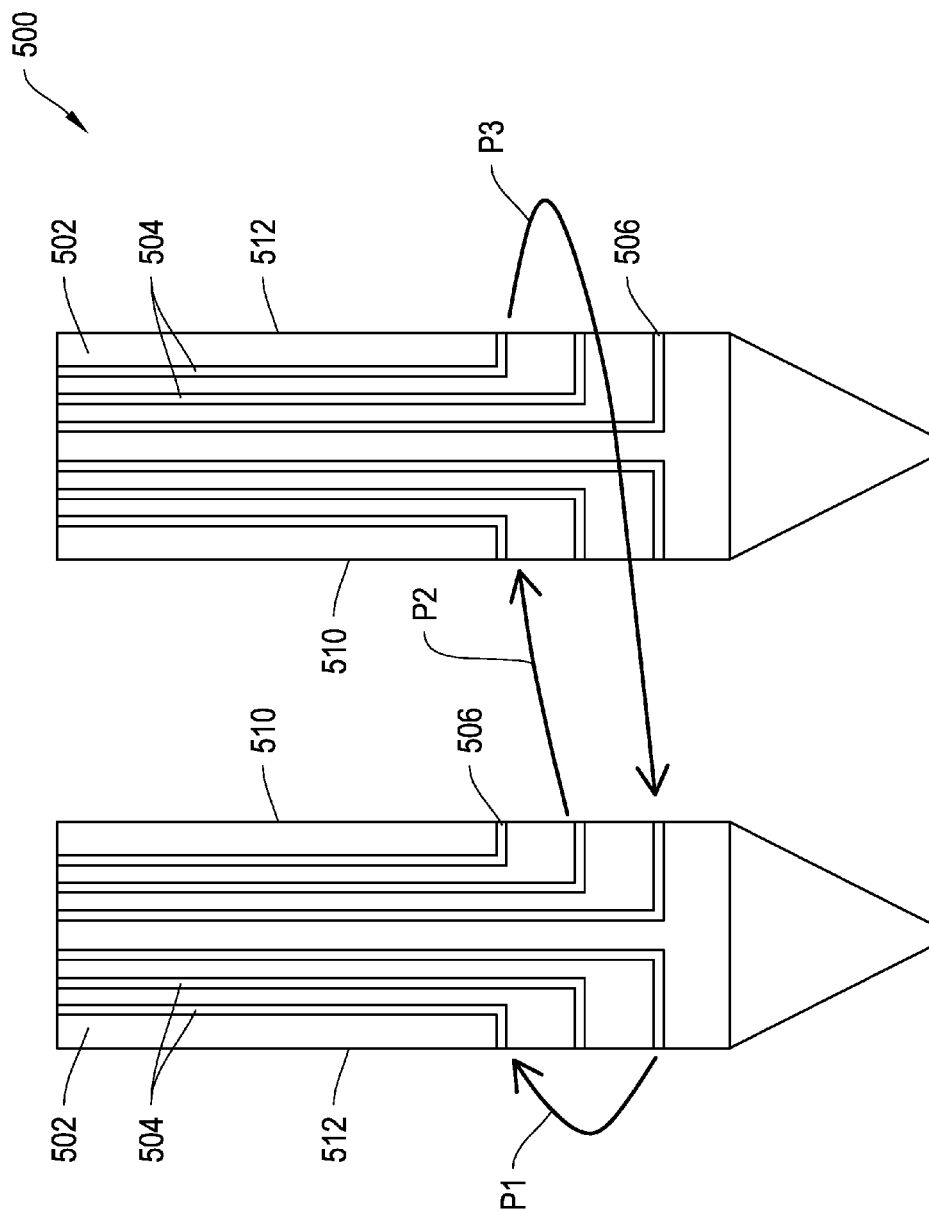
FIG. 5 is a schematic front view of paths corresponding to the travel of light around a pair of optrode shanks, in accordance with one embodiment of the invention.

FIG. 5 depicts an optrode 500 and paths corresponding to the travel of light around the optrode 500, in accordance with certain embodiments of the invention. Each shank 502 of the optrode 500 includes a plurality of internal waveguides 504 and apertures 506 associated with the waveguides 504. Some of the apertures 506 are arranged on inner surfaces 510 of the shanks 502. Other apertures 506 are arranged on outer surfaces 512 of the shanks 502. In general, light emitted by one aperture 506 may be received by any one of the other apertures 506. For example, light following a path P1 is emitted from an aperture 506 on one side of a shank 502 and received by a different aperture 506 on the same side of the shank 502. Similarly, light following a path P2 is emitted from an aperture 506 on the inner surface 510 of one shank 502 and received by an aperture 506 on the inner surface 510 of the other shank 502. Further, light following path P3 is emitted from an aperture 506 on an outer surface 512 of one shank 502 and received by an aperture 506 on an inner surface 510 of the other shank 502. In various embodiments, light emitted by an aperture 506 is diffused by the adjacent neural tissue in all directions, thereby allowing the light to be received by any other aperture 506 of the optrode 500.

Figure 6:
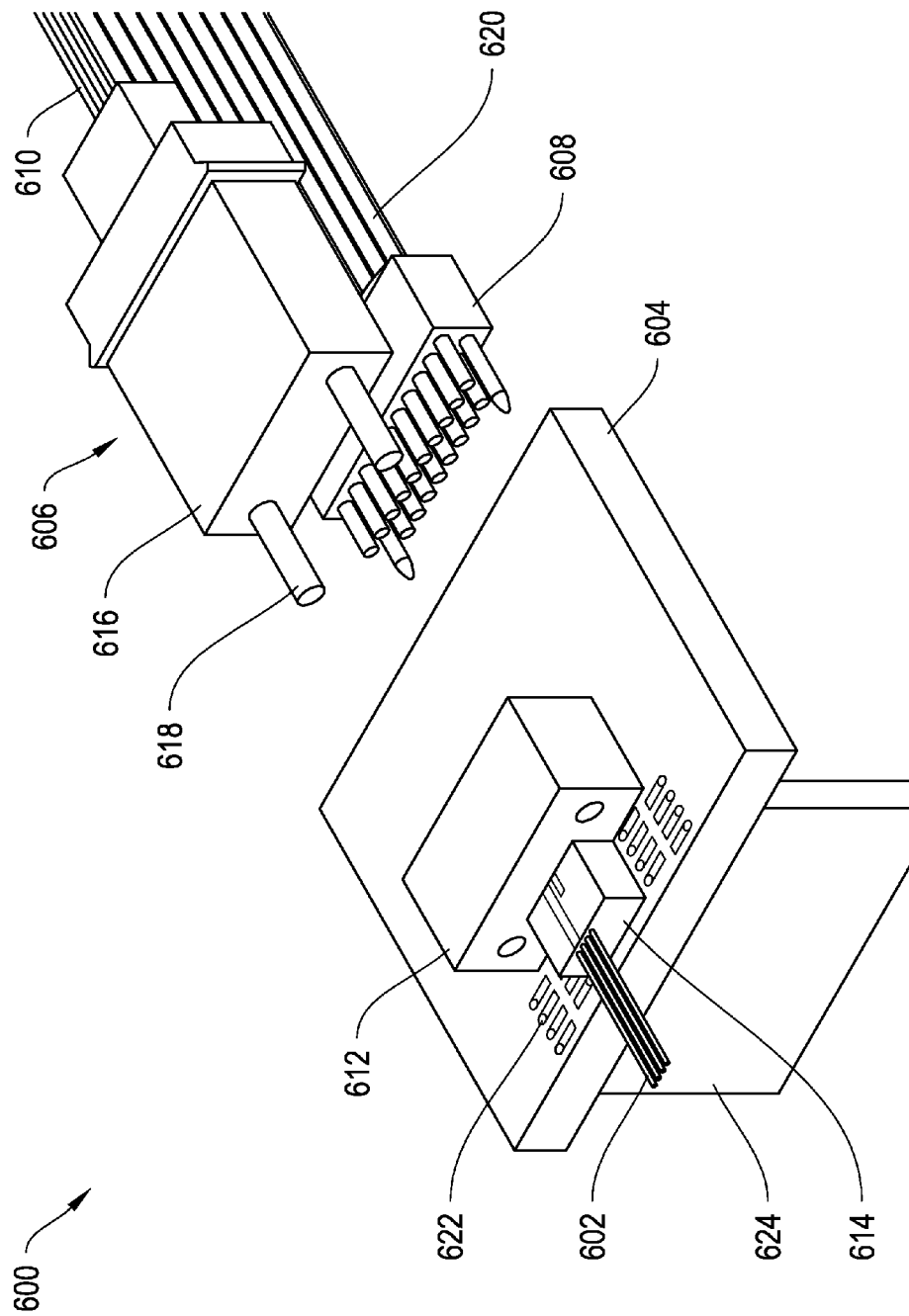
FIG. 6 is a schematic perspective view of optical and electrical connections for an optrode system, in accordance with one embodiment of the invention.

FIG. 6 is a perspective view of optical and electrical connections for an optrode system 600, in accordance with certain embodiments of the invention. The optrode system 600 includes an optrode 602, a printed circuit board 604, a waveguide coupler 606, and an electrical connector 608. Light is delivered to and from the optrode 602 using the waveguide coupler 606 and an optical cable 610. The waveguide coupler 606 includes a fixed portion 612 that is butted up against the optrode 602. An alignment block 614 aligns the internal waveguides of the optrode 602 with the fixed portion 612 of the waveguide coupler 606. The waveguide coupler 606 also includes a detachable portion 616 that may be disconnected from the fixed portion 612, as shown. Alignment pins 618 on the detachable portion 616 ensure the detachable portion 616 and the fixed portion 612 are properly aligned when connected.

Electrical power and/or signals are transmitted to and from the optrode 602 using the electrical connector 608 and an electrical cable 620. The electrical connector 608 may be connected or disconnected from a receptacle (not shown) on the printed circuit board 604. Contacts 622 on the optrode 602 and/or on the printed circuit board 604 allow electricity to be transmitted between the optrode 602 and the printed circuit board 604. A head mount 624 allows the optrode system 600 to be fixed or attached to an object, such as an animal.

Figure 7:
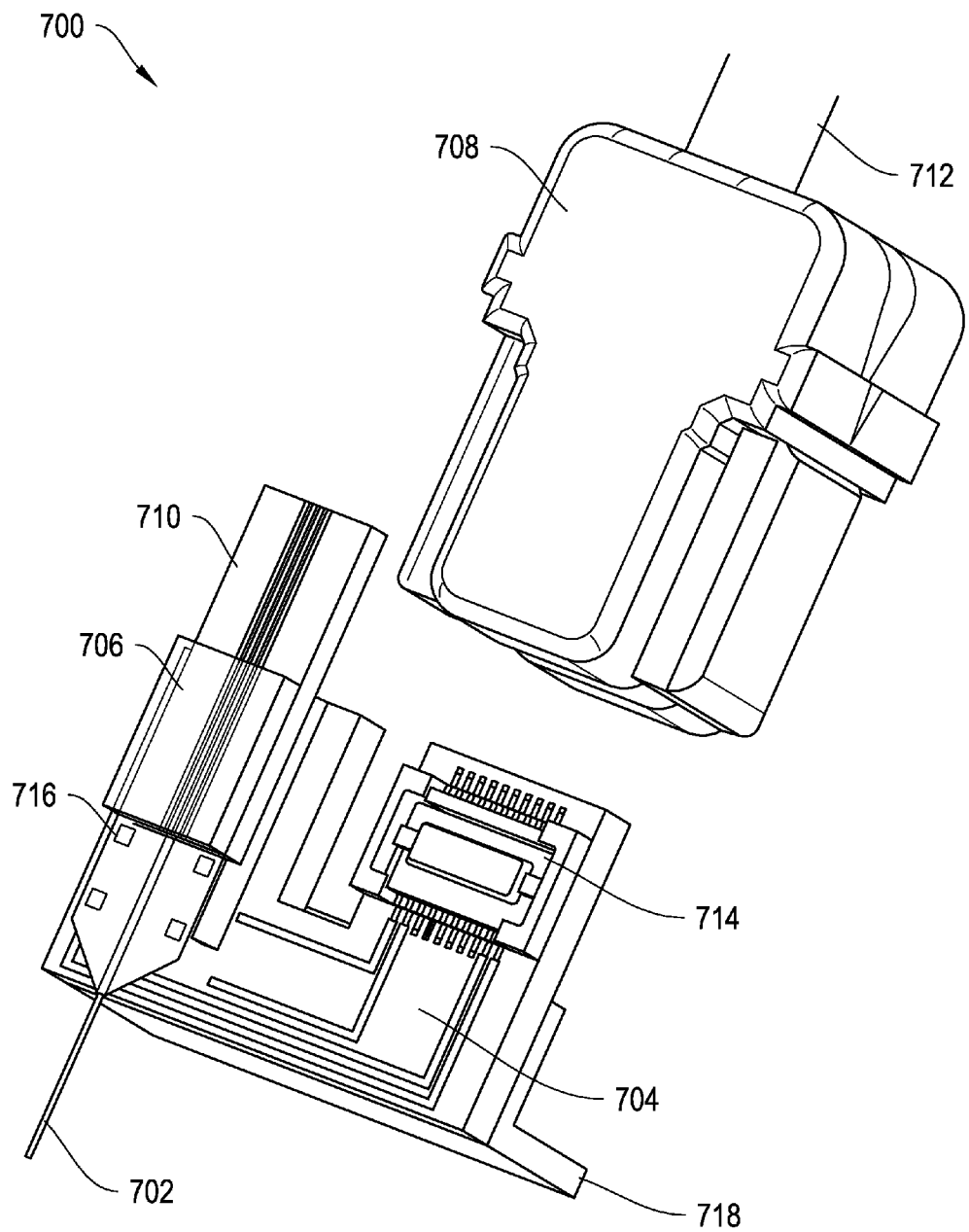
FIG. 7 is a schematic perspective view of optical and electrical connections for an optrode system, in accordance with one embodiment of the invention.

FIG. 7. is a perspective view of optical and electrical connections for an optrode system 700, in accordance with certain embodiments of the invention. The optrode system 700 includes an optrode 702, a printed circuit board 704, a waveguide coupler 706, and an electrical connector 708. Light is delivered to and from the optrode 702 using the waveguide coupler 706 and an optical cable 710. The waveguide coupler 706 may be a V-groove optical interface coupler, which may be detachable. Electrical power and/or signals are transmitted to and from the optrode 702 using the electrical connector 708 and an electrical cable 712. The electrical connector 708 may be connected or disconnected (as shown) from a clip 714 attached to the printed circuit board 704. Contacts 716 on the optrode 702 and/or printed circuit board 704 allow electricity to be transmitted between the optrode 702 and the printed circuit board 704. In one embodiment, contacts 716 on the optrode 702 are wire-bonded to the printed circuit board 704. A head mount 718 allows the optrode system 700 to be fixed or attached to an object, such as an animal.

In certain embodiments, a method of manufacturing an optrode includes embedding internal waveguides and electrodes into shanks of the optrode using photolithographic techniques. For example, in one embodiment, an optrode fabrication process begins with a silicon on insulator (SOI) wafer. The SOI wafer may include a silicon device layer on the order of 20 microns thick, bonded to a silicon handle wafer with an oxide layer. A lower cladding layer of a low index optical polymer may be spun on the SOI wafer and then cured. A high index core layer may then be spun on top of the cladding layer. In certain embodiments, the internal waveguides are defined using a photolithographic process and/or a photolithographic plus etch process. End facets and/or turning mirrors may not be fabricated at this time. A lower index polymer for the upper cladding may then be spun on, possibly in several steps, until a planar surface is created that is sufficiently higher than the core layer. Next, a metal pattern may be defined, either by additive or subtractive processes, which will delineate the end facets of the waveguides, any turning mirrors, and an etch of silicon prongs. These features may then be dry etched, and an etch mask may be removed. Lastly, the silicon handle wafer may be dissolved or ground, yielding the silicon shanks or prongs with the internal waveguides. Additional suitable fabrication processes for the internal waveguides may include micro-opto-electro-mechanical systems (MOEMS) processes, microembossing, thermal nanoimprint lithography (NIL), and/or combined nanoimprinting and photolithography (CNP).

Figure 8A:
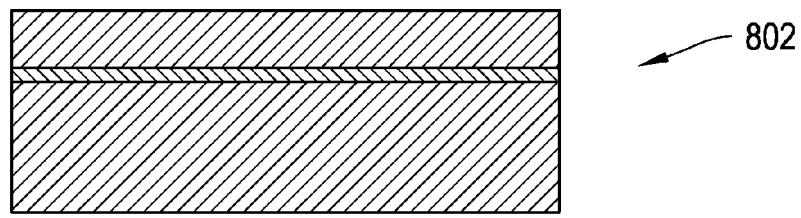
FIGS. 8a through 8g are schematic cross-sectional views of a method of manufacturing an optrode, in accordance with one embodiment of the invention.
Figure 8B:
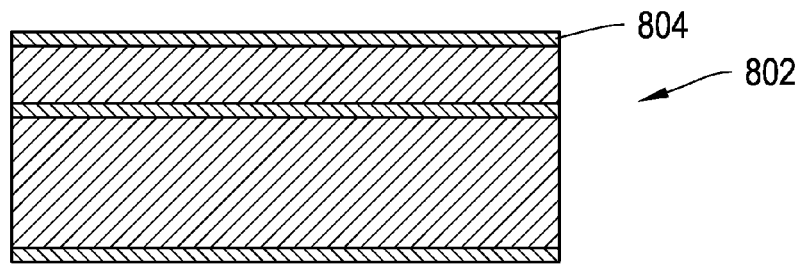
Figure 8C:
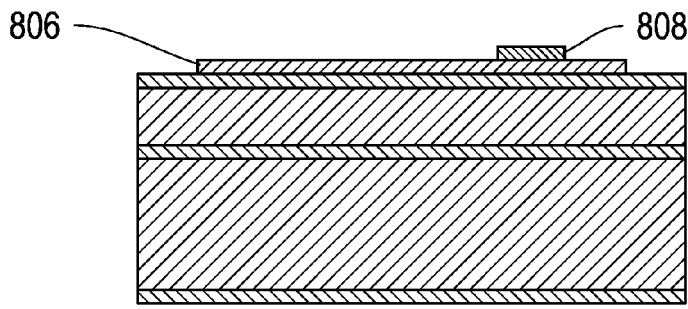
Figure 8D:
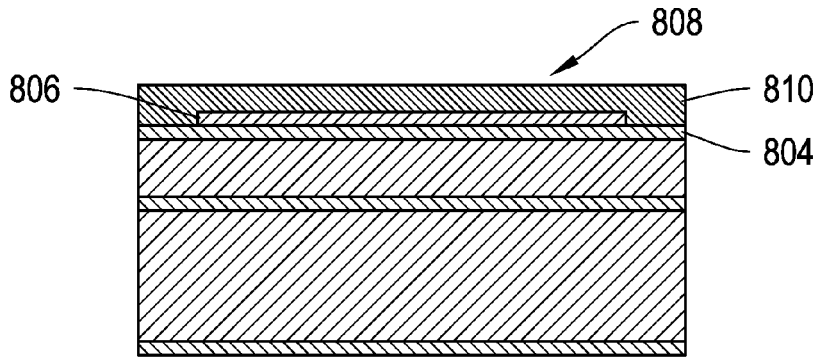
Figure 8E:
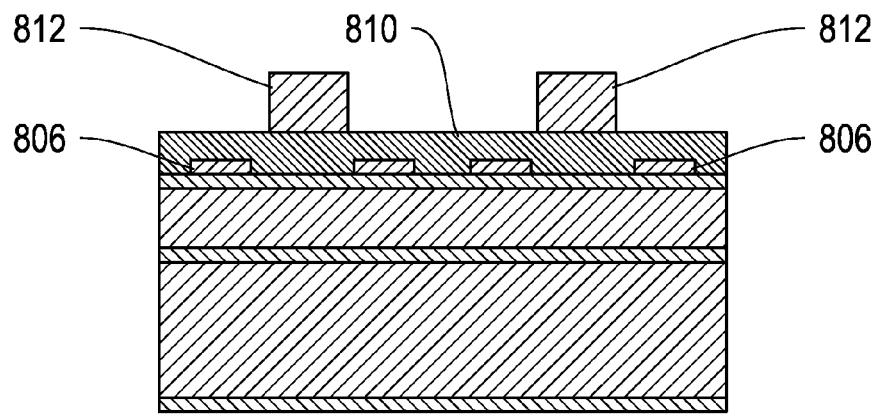
Figure 8F:
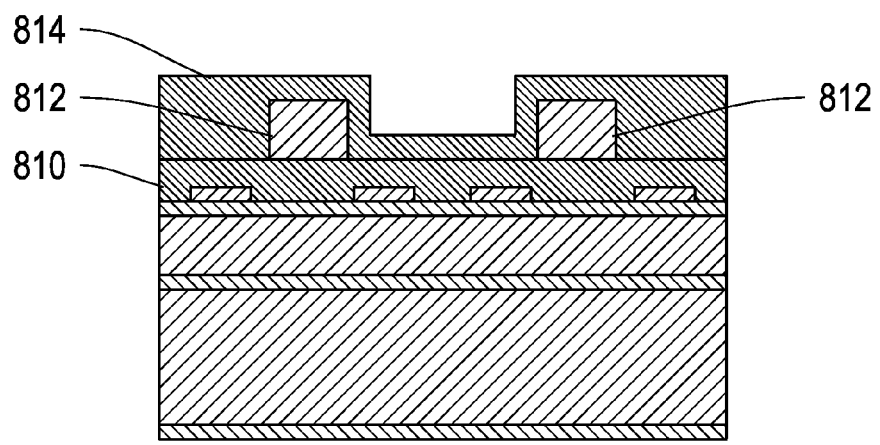
Figure 8G:
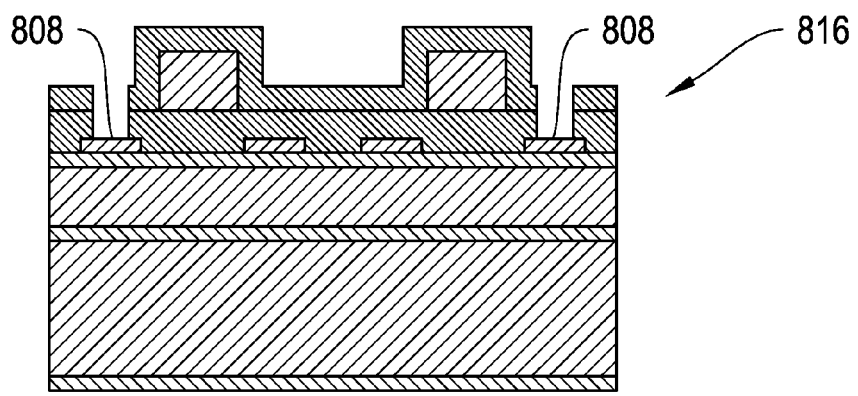

FIGS. 8a through 8g are schematic views of a method of manufacturing an optrode, in accordance with various embodiments of the invention. Referring to FIG. 8a, the method begins with a starting substrate 802, such as a silicon on insulator (SOI) substrate. A thermal oxide insulation layer 804 is then grown on the starting substrate 802 (FIG. 8b). Interconnects 806 (e.g., Cr/Au) and electrodes or recording sites 808 (e.g., Ti/Pt) are deposited and patterned using two-step lithography (FIG. 8c). A lower cladding layer 810 (e.g., PDMS) is deposited onto the insulation layer 804, the interconnects 806, and the recording sites 808 (FIG. 8d). A waveguide core 812 made of, for example, polyimide or SU-8 is deposited and patterned over the lower cladding layer 810 and the interconnects 806 (FIG. 8e). An upper cladding layer 814 is then deposited onto the patterned waveguide core 812 and the lower cladding layer 810 (FIG. 8O. Finally, the recording sites 808 and bond pads 816 are opened (FIG. 8g).

Figure 8H:
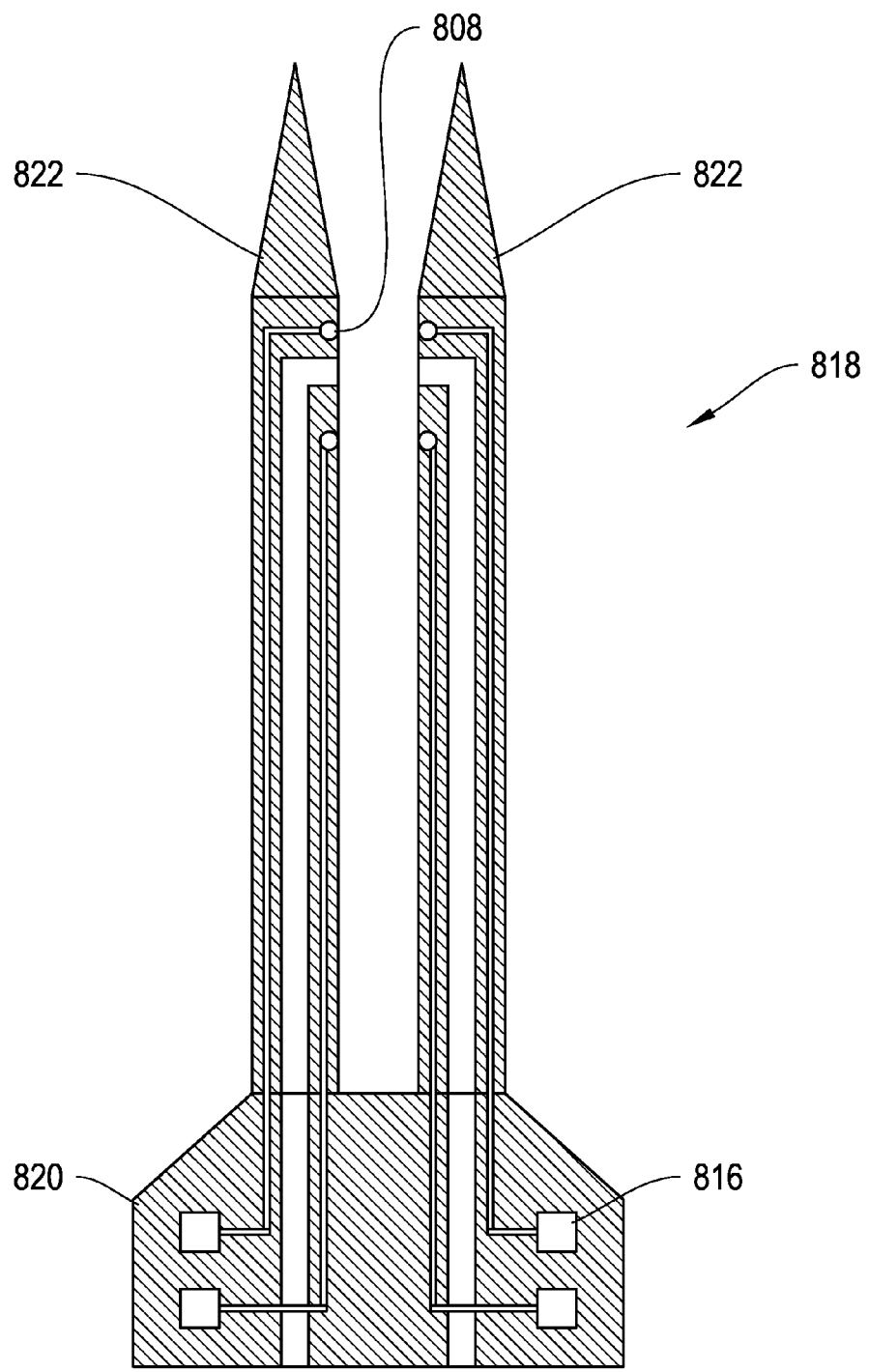
FIG. 8h is a schematic top view of an optrode produced by the method of FIGS. 8a through 8g, in accordance with one embodiment of the invention.

FIG. 8h depicts an optrode 818 produced by the method. In the depicted embodiment, the bond pads 816 are located on a tab or base portion 820 of the optrode 818 while the recording sites 808 are located on a pair of shanks 822 of the optrode 818. In one embodiment, the bond pads 816 include a gold coating and the recording sites 808 include a platinum or iridium coating.

Figure 9A:
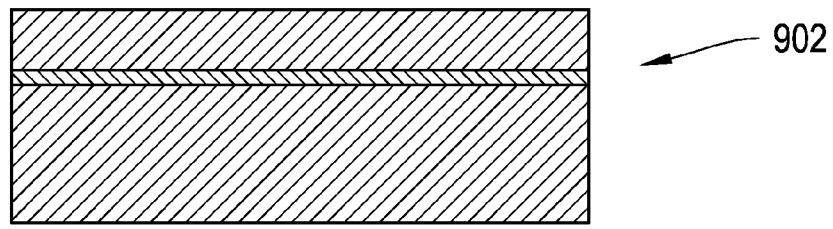
FIGS. 9a through 9g are schematic cross-sectional views of a method of manufacturing an optrode, in accordance with one embodiment of the invention.
Figure 9B:
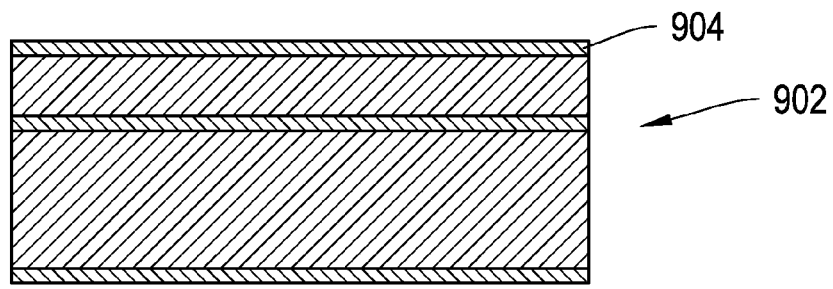
Figure 9C:
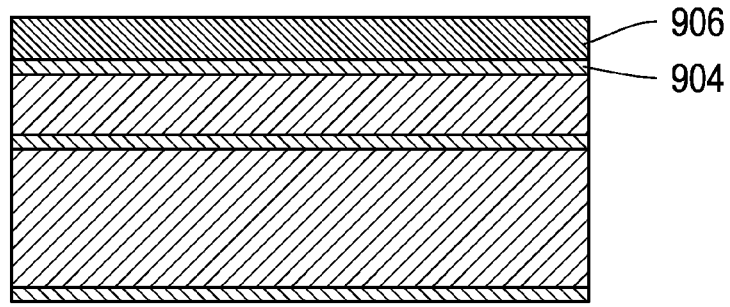
Figure 9D:
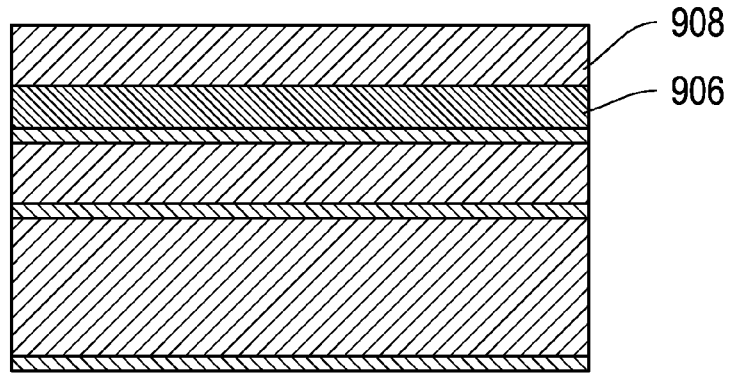
Figure 9E:
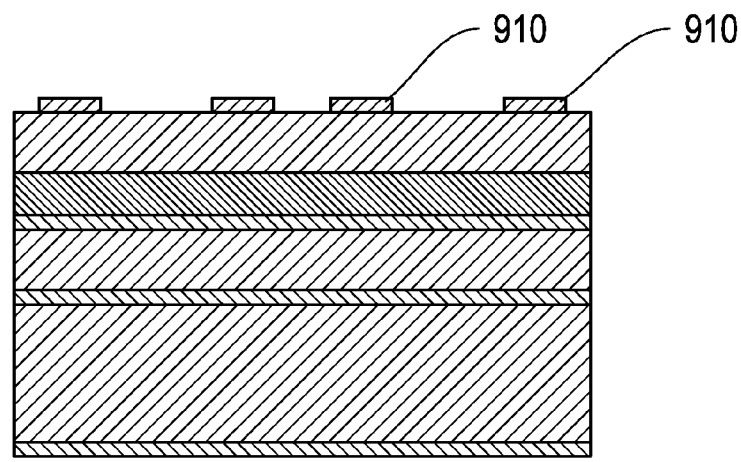
Figure 9F:
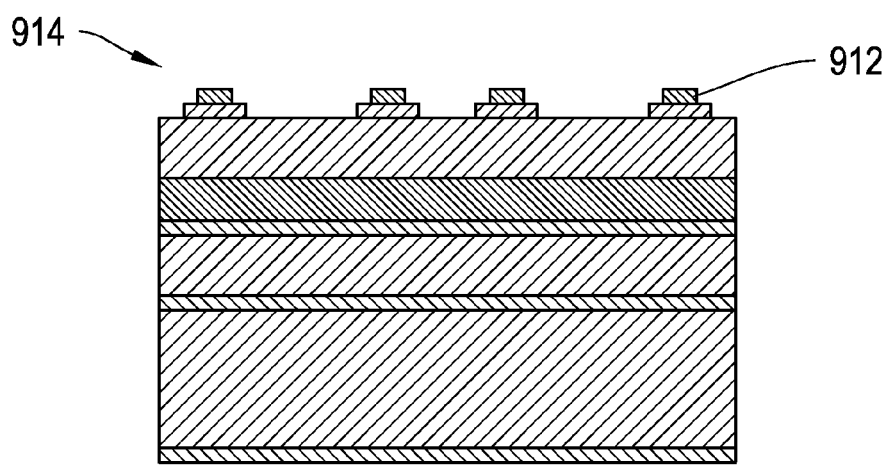
Figure 9G:
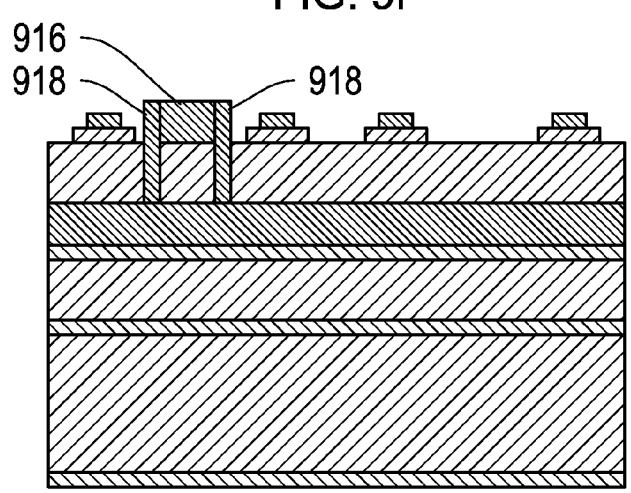

FIGS. 9a through 9g are schematic views of another method of manufacturing an optrode, in accordance with various embodiments of the invention. Referring to FIG. 9a, the method begins with a starting substrate 902, such as a silicon on insulator (SOI) substrate (e.g., four inch). A thermal oxide insulation layer 904 is then grown on the starting substrate 902 (FIG. 9b). A lower cladding layer 906 (e.g., PDMS) is deposited onto the insulation layer 904 (FIG. 9c). A waveguide core 908 made of, for example, polyimide or SU-8 is deposited onto the lower cladding layer 906 (FIG. 9d). Next, interconnects 910 (e.g., of Cr/Au) are deposited and patterned (FIG. 9e), followed by recording sites 912 (e.g., of Ti/Pt) and bond pads 914 (FIG. 9f), and an upper cladding layer 916 (FIG. 9g). Finally, as also shown in FIG. 9g, waveguide cladding materials 918 are patterned and processed using reactive-ion etching (RIE).

Figure 9H:
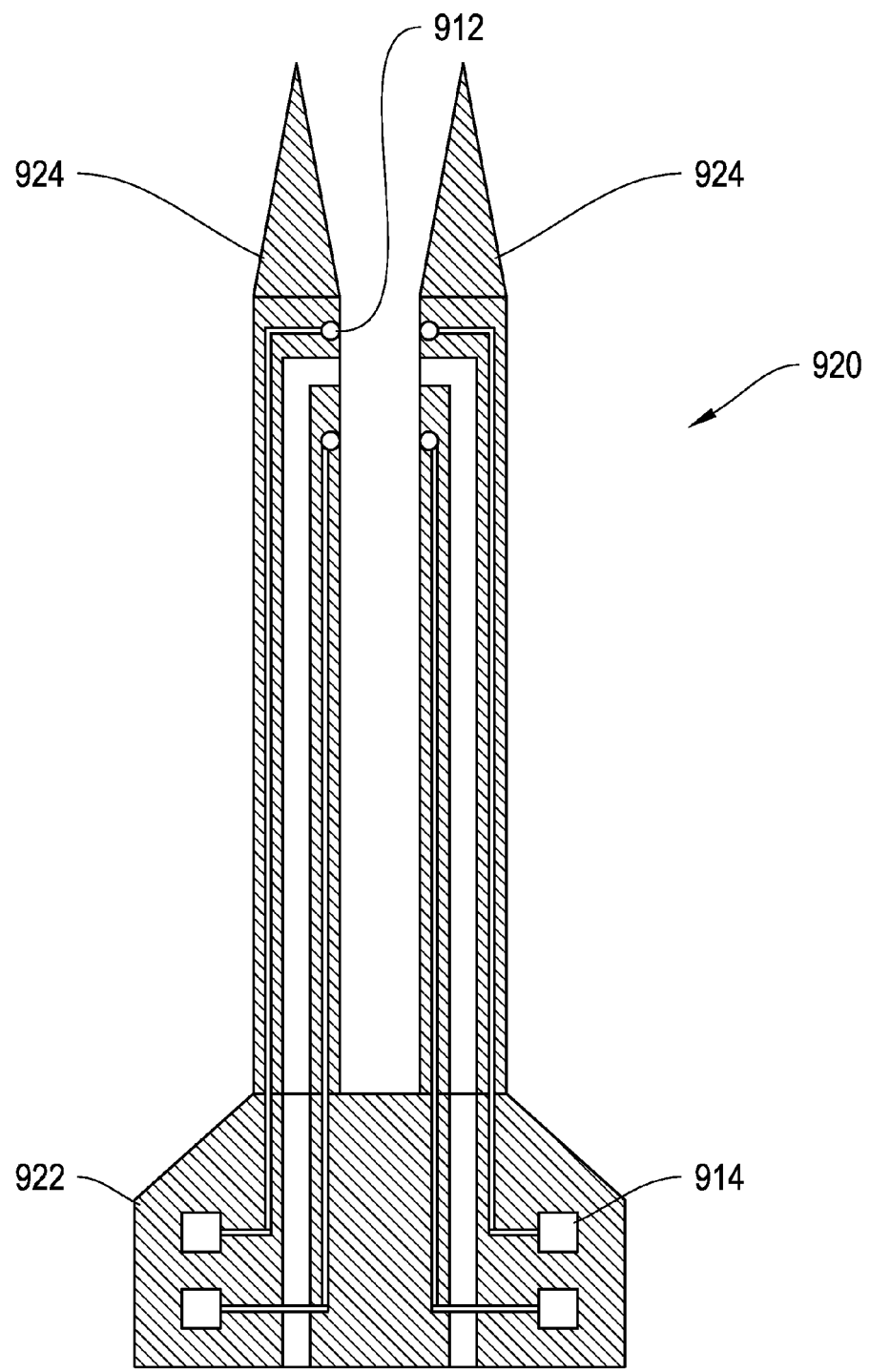
FIG. 9h is a schematic top view of an optrode produced using the method of FIGS. 9a through 9g, in accordance with one embodiment of the invention.

FIG. 9h depicts an optrode 920 produced by the method. In the depicted embodiment, the bond pads 914 are located on a tab or base portion 922 of the optrode 920 while the recording sites 912 are located on a pair of shanks 924 of the optrode 920. In one embodiment, the bond pads 914 include a gold coating and the recording sites 912 include a platinum or iridium coating.

In general, by incorporating both optical and electrical components into the optrode, the optrode advantageously enables optical interrogation and spectroscopy of surrounding tissues with substantially simultaneous electrical recording of neurons and bioimpedance functions. As described above, the waveguide apertures transmit and collect light for optical analysis. Localized apertures and recording electrodes may be used to target specific areas.

In certain embodiments, the optical measurements are used to monitor tissue damage that occurs due to implantation of a probe such as the optrode. For example, insertion of a probe may cause cell death (both glial and neuronal), mechanical tissue compression, a collection of debris resulting from cell death, and severed neuronal processes and blood vessels. Long term implantation of the probe may trigger a foreign body response, primarily affected by microglia and astrocytes. Scar tissue may buildup in the vicinity of the probe. By optically interrogating the neural tissue, the optrode allows the health of the tissue to be monitored over time.

In various embodiments, light received by the photo-detector 106 is analyzed to determine the behavior or health of neural tissue. Analysis techniques that may be utilized include, for example, optical spectroscopy and near-infrared spectroscopy. In some embodiments, a spectroscopic technique includes exposing tissue to different wavelengths of light and evaluating the wavelengths of light received from the tissue. In general, the tissue may absorb or scatter light as a function of wavelength. For example, the tissue may include chromophores that cause one wavelength to be preferentially scattered or absorbed. Based on the spectrum of light received from the tissue, various characteristics of the tissue may be inferred, such as the tissue health, tissue density, and/or a size distribution (e.g., of cells in the tissue).

In some embodiments, the optrode is used to remove scar tissue buildup that has occurred around the optrode. The scar tissue may prevent proper functioning of the optrode by, for example, interfering with the flow of electricity between the tissue and the optrode. In one embodiment, the optrode is used to remove scar tissue by performing optical ablation. The optical ablation may be performed by emitting a high-intensity light (e.g., laser light) from the optrode to burn away adjacent scar tissue. After removing the scar tissue, proper functioning of the optrode may be restored.

In certain embodiments, the optrode is configured to stimulate and record neuron activity both optically and electrically. For example, electrical stimulation and/or optical stimulation may cause an increase, decrease, or block of neuronal activity, and the neural response to the stimulation may be detected and recorded using the electrical components and/or the optical components of the optrode.

Having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A transmissive spectroscopic probe, comprising:
   a first shank comprising light transmitting optical components disposed within the first shank and configured to transmit light into a sample and towards a second shank of the probe;
   the second shank spaced between about 20 microns and 1000 microns away from the first shank and comprising light receiving optical components disposed within the second shank and configured to collect at least a portion of the light transmitted into the sample by the light transmitting optical components; and
   electrical components disposed within at least one of the first shank and the second shank for recording an electrical signal from the sample.

2. The probe of claim 1, further comprising at least one waveguide for transmitting light through the first shank and/or the second shank.

3. The probe of claim 2, wherein the at least one waveguide comprises a photodefinable polymer.

4. The probe of claim 1, wherein the light transmitting and light receiving optical components are each in optical communication with at least one aperture defined by the first shank and the second shank.

5. The probe of claim 1, wherein the electrical components comprise an electrode.

6. The probe of claim 1, wherein a separation distance between the first shank and the second shank is about 100 microns.

7. The probe of claim 1, wherein the first shank and the second shank have a width and a depth, each of which is between about 10 microns and about 100 microns.

8. The probe of claim 7, wherein the width is about 25 microns and the depth is about 10 microns.

9. The probe of claim 1, wherein the electrical components are further configured to apply a voltage to the sample.

10. The probe of claim 1, wherein the sample comprises neural tissue.

11. A system, comprising:
   a light source;
   a probe comprising:
   i) a first shank comprising:
      light transmitting optical components configured to transmit light into a sample;
   ii) a second shank spaced between about 20 microns and 1000 microns away from the first shank and comprising:
      light receiving optical components configured to collect light from the sample; and
   iii) electrical components disposed within the first shank and the second shank for recording an electrical signal from the sample;
   a photo-detector;
   a plurality of external waveguides for transmitting light from the light source to the probe and from the probe to the photo-detector; and
   a controller configured to spectrographically analyze a light signal collected by the second shank.

12. The system of claim 11, wherein the electrical components are further configured to apply a voltage to the sample.

* * * * *